United States Patent [19]

Holloway et al.

[11] Patent Number: 5,502,078
[45] Date of Patent: Mar. 26, 1996

[54] CHEMICAL COMPOUNDS

[75] Inventors: Brian R. Holloway, Congleton; Ralph Howe, Macclesfield; Balbir S. Rao, Chapel, all of England

[73] Assignee: Zeneca Limited, London, England

[21] Appl. No.: 57,763

[22] Filed: May 7, 1993

Related U.S. Application Data

[63] Continuation-in-part of Ser. No. 889,186, May 28, 1992, abandoned.

[30] Foreign Application Priority Data

May 28, 1991 [GB] United Kingdom .................... 9111425

[51] Int. Cl.$^6$ .................................................. A61K 31/195
[52] U.S. Cl. ........................... 514/567; 514/539; 562/451; 560/42
[58] Field of Search .............................. 560/42; 562/451; 514/567, 539

[56] References Cited

U.S. PATENT DOCUMENTS

| | | |
|---|---|---|
| 3,816,516 | 6/1974 | Cox . |
| 4,329,358 | 5/1982 | Ainsworth et al. . |
| 4,478,849 | 10/1984 | Ainsworth et al. ...................... 424/285 |
| 4,772,631 | 9/1988 | Holloway et al. . |
| 4,977,148 | 12/1990 | Holloway . |
| 4,999,377 | 3/1991 | Caulkett et al. . |
| 5,002,946 | 8/1991 | Manara et al. ....................... 514/230.8 |

FOREIGN PATENT DOCUMENTS

| | | |
|---|---|---|
| 0006735 | 1/1980 | European Pat. Off. . |
| 0021636 | 1/1981 | European Pat. Off. . |
| 0023385 | 2/1981 | European Pat. Off. . |
| 0025331 | 3/1981 | European Pat. Off. . |
| 0040000 | 11/1981 | European Pat. Off. . |
| 0063004 | 10/1982 | European Pat. Off. . |
| 0061907 | 10/1982 | European Pat. Off. . |
| 0403360 | 6/1990 | European Pat. Off. . |
| 1245148 | 9/1971 | United Kingdom . |
| 2212801 | 8/1989 | United Kingdom . |
| 9013533 | 11/1990 | WIPO . |
| WO9013535 | 11/1990 | WIPO . |

*Primary Examiner*—Paul F. Shaver
*Assistant Examiner*—Samuel Barts
*Attorney, Agent, or Firm*—Cushman Darby & Cushman

[57] ABSTRACT

Compounds of the formula (I):

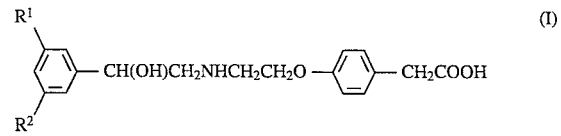

and bioprecursors and pharmaceutically acceptable salts thereof are described as $\beta_3$-adrenoceptor agonists having anti-obesity, hypoglycaemic and related therapeutic utilities. Processes for their preparation are described as are compositions containing them.

9 Claims, No Drawings

CHEMICAL COMPOUNDS

This application is a continuation-in-part of Ser. No. 07/889,186, filed May 28, 1992, now abandoned.

The present invention relates to 2-hydroxy-2-phenyl-ethylamino compounds and in particular to such compounds containing a phenylacetyl group. This invention further relates to processes and intermediates for their preparation, to their use in methods of therapy and to pharmaceutical compositions containing them. The compounds of the present invention are $\beta_3$-adrenoceptor agonists and are of value in disease conditions mediated through such adrenoceptors. Administration of the compounds of this invention to warm-blooded animals provides a thermogenic effect, that is thermogenesis is stimulated and administration of the compounds is of use, for example, in the treatment of obesity and related conditions such as mature onset diabetes associated with obesity. In addition, the compounds of this invention improve glucose tolerance in warm-blooded animals and are of use in combatting disease conditions wherein such activity is beneficial for example they have hypoglycaemic activity. The compounds of this invention may also be used in the treatment of non-insulin dependent diabetes mellitus (NIDDM) and in conditions wherein insulin resistance is of importance such as hypertension, hyperlipidaemia and decreased fibrinolysis (Reaven's syndrome or Syndrome X).

Accordingly the present invention provides compounds of the formula (I):

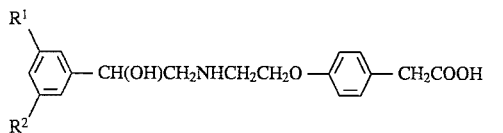

wherein $R^1$ is chloro, fluoro, bromo, trifluoromethyl or methyl; $R^2$ is hydrogen or fluoro; or a bioprecursor or a pharmaceutically acceptable salt thereof.

Suitably $R^1$ is chloro, bromo or fluoro. In another aspect $R^1$ is trifluoromethyl.

Preferably $R^2$ is hydrogen.

In one aspect $R^1$ is chloro or methyl and $R^2$ is hydrogen. In a further aspect $R^1$ is trifluoromethyl and $R^2$ is hydrogen.

In a preferred aspect $R^1$ is chloro and $R^2$ is hydrogen.

In another preferred aspect $R^1$ is bromo and $R^2$ is hydrogen.

Favourably the compounds of the formula (I) are in the form of a carboxylic acid or a pharmaceutically acceptable salt thereof. These compounds are amphoteric and may be used in the zwitterionic form, or as a pharmaceutically acceptable acid addition salt, or as a salt with a base affording a pharmaceutically acceptable cation. Particular examples of pharmaceutically acceptable acid-addition salts include, for example, salts with inorganic acids such as hydrohalides (especially hydrochlorides or hydrobromides), sulphates and phosphates, and salts with organic acids such as succinates, citrates, lactates, tartrates and salts derived from acidic water-soluble polymers. Particular examples of salts with bases affording a pharmaceutically acceptable cation include, for example, alkali metal and alkaline earth metal salts, such as sodium, potassium, calcium and magnesium salts, and ammonium salts and salts with suitable organic bases such as triethanolamine.

Bioprecursors are those pharmaceutically acceptable compounds that are degraded in the animal body to produce the parent acid. Such compounds can be identified by administering, for example orally to a test animal, the compound under test and subsequently examining the test animal's body fluids.

One class of bioprecursor is that of the corresponding ester bioprecursors of the carboxy group in the compounds of the formula (I). Suitable esters include $C_{1-6}$alkyl esters, for example, methyl and ethyl.

Another class of bioprecursor is that of the corresponding ester bioprecursors of the hydroxy group. Such esters include, as their acyl group, for example, acetyl, propionyl, pivaloyl, $C_{1-4}$alkoxycarbonyl for example ethoxycarbonyl and phenylacetyl. In particular the acetyl group is suitable.

A further class of bioprecursor is that of the corresponding amide bioprecursors of the carboxy group in the compounds of the formula (I). Suitable amides include, for example, amides of the formula $-CONR^3R^4$, wherein $R^3$ and $R^4$ are independently hydrogen, $C_{1-6}$alkyl, hydroxy$C_{2-6}$alkyl (wherein the hydroxy substituent is on other than the α-carbon), $C_{1-4}$alkoxy$C_{1-6}$alkyl, phenylalkyl, allyl, cyclopropyl or cyclopentyl or the group $-NR^3R^4$ is morpholino, piperidino or pyrrolidino. In general amides, in particular wherein $R^3$ and $R^4$ are independently hydrogen, are primarily viewed as intermediates for the preparation of the corresponding carboxylic acid or ester.

A preferred class of bioprecursors is that of the formula (II):

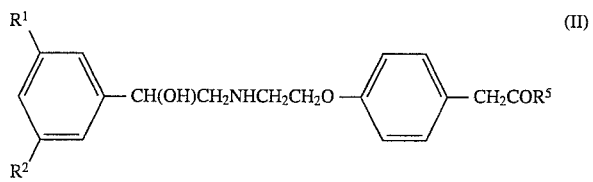

wherein $R^1$ and $R^2$ are as hereinbefore defined and $R^5$ is $C_{1-6}$alkoxy for example methoxy.

Bioprecursors of the compounds of the formula (I) may have a thermogenic effect in their own right and this is another aspect of the invention.

Particular compounds of the invention are:
(R)-methyl 4-[2-(2-hydroxy-2-(3-trifluoromethylphenyl)ethylamino)ethoxy]phenylacetate,
(R)-4-[2-(2-hydroxy-2-(3-trifluoromethylphenyl)ethylamino)ethoxy]phenylacetic acid,
methyl 4-[2-(2-[3-chlorophenyl]-2-hydroxyethylamino)ethoxy]phenylacetate hydrochloride,
4-[2-(2-[3-chlorophenyl]-2-hydroxyethylamino)ethoxy] phenylacetic acid, methyl-4-[2-(2-[3-fluorophenyl]-2-hydroxyethylamino)ethoxy]phenylacetate hydrochloride,
4-[2-(2-[3-fluorophenyl]-2-hydroxyethylamino)ethoxy]phenylacetic acid, methyl 4-[2-(2-[3-bromophenyl]-2-hydroxyethylamino)ethoxy]phenylacetate hydrochloride,
4-[2-(2-[3-bromophenyl]-2-hydroxyethylamino)ethoxy] phenylacetic acid, 4-[2-(2-[3,5-difluorophenyl]-2-hydroxyethylamino)ethoxy]phenylacetic acid,
4-[2-(2-hydroxy-2-(3-methylphenyl)ethylamino)ethoxy] phenylacetic acid and pharmaceutically acceptable salts thereof.

It will be appreciated that the compounds of the formula (I) and bioprecursors thereof contain one or more asymmetric carbon atoms and can exist as optically active enantiomers or as optically inactive racemates. The present invention encompasses any enantiomer, racemate and/or (when two or more asymmetric carbon atoms are present) diastereoisomer, which when administered in a therapeutic amount provides a thermogenic effect in warm-blooded animals, it being well known in the chemical art how to prepare individual enantiomers, for example by resolution of the racemate or by stereospecific synthesis, and how to determine the thermogenic properties, for example, using the standard tests described hereinafter. It is preferred that the compounds of the present invention are provided in the (R) absolute configuration, at the —CH(OH)— group, (under the Cahn-Prelog-Ingold rules).

In order to use a compound of the present invention or a pharmaceutically acceptable salt thereof for the therapeutic treatment of warm-blooded mammals including humans, in particular for treating obesity, it is normally formulated in accordance with standard pharmaceutical practice as a pharmaceutical composition.

Therefore in another aspect the present invention provides a pharmaceutical composition which comprises a compound of the formula (I) or a bioprecursor thereof or a pharmaceutically acceptable salt thereof and a pharmaceutically acceptable carrier.

The pharmaceutical compositions of this invention may be administered in standard manner for example by oral or parenteral administration. For these purposes they may be formulated by means known to the art into the form of, for example, tablets, capsules, pills, powders, aqueous or oily solutions or suspensions, emulsions, and sterile injectable aqueous or oily solutions or suspensions.

In general compositions for oral administration are preferred.

The compositions may be obtained using standard excipients and procedures well known in the art. A unit dose form such as a tablet or capsule will usually contain, for example 0.1–500 mg of active ingredient, more suitably 10–250 mg, and preferably 50–100 mg of the compound of this invention.

The compositions may also contain other active ingredients known for use in the disease condition to be treated, for example appetite suppressants, vitamins, antihypertensives and hypoglycaemic agents such as sulphonylureas, biguanides and thiazolidinediones. It is understood that such compositions cover co-formulation, concurrent and sequential therapy of the two or more active ingredients.

In one aspect of the present invention, a compound of the formula (I) or a bioprecursor thereof may be formulated for oral administration in a sustained (or delayed) release composition, for example a matrix tablet formulation comprising insoluble or swellable polymeric filler, or a coated spheroid formulation.

When used to produce thermogenic effects in warm-blooded animals including man, a compound of the formula (I) or a bioprecursor thereof or a pharmaceutically acceptable salt thereof as appropriate, will be administered so that a dose in the general range 0.002–20 mg/kg, suitably in the range 0.02–10 mg/kg, and preferably in the range 0.5–5 mg/kg is administered daily, given in a single dose or divided doses as necessary, typically one to three times a day. However, it will be appreciated by those skilled in the art that dosage will necessarily be varied as appropriate, depending on the severity of the condition under treatment and on the age and sex of the patient and according to known medical principles.

In addition the compounds of the present invention lower triglyceride levels and cholesterol levels and raise high density lipoprotein (HDL) levels and are therefore of use in combatting medical conditions wherein such lowering (and raising) is thought to be beneficial. Thus they may be used in the treatment of hypertriglyceridaemia, hypercholesterolaemia and conditions of low HDL levels in addition to the treatment of atherosclerotic disease such as of coronary, cerebrovascular and peripheral arteries, cardiovascular disease and related conditions.

Accordingly in another aspect the present invention provides a method of lowering triglyceride and/or cholesterol levels and/or increasing HDL levels which comprises administering, to an animal in need thereof, a therapeutically effective amount of a compound of the formula (I) or a bioprecursor thereof or pharmaceutically acceptable salt thereof. In a further aspect the present invention provides a method of treating atherosclerosis which comprises administering, to an animal in need thereof, a therapeutically effective amount of a compound of the formula (I) or a bioprecursor thereof or pharmaceutically acceptable salt thereof. The compositions are formulated and administered in the same general manner as detailed above for producing a thermogenic effect. They may also contain other active ingredients known for use in the treatment of atherosclerosis and related conditions, for example fibrates such as clofibrate, bezafibrate and gemfibrozil; inhibitors of cholesterol biosynthesis such as HMG-CoA reductase inhibitors for example lovastatin, simvastatin and pravastatin; inhibitors of cholesterol absorption for example beta-sitosterol and (acyl CoA:cholesterol acyltransferase) inhibitors for example melinamide; anion exchange resins for example cholestyramine, colestipol or a dialkylaminoalkyl derivative of a cross-linked dextran; nicotinyl alcohol, nicotinic acid or a salt thereof; vitamin E; and thyromimetics.

In a further aspect the compounds of the present invention stimulate the "atypical" β-adrenoceptors in the gastrointestinal tract and therefore inhibit gastrointestinal motility. They may be of use in combatting medical conditions wherein stimulation of "atypical" β-adrenoceptors in the gastrointestinal tract is thought to be beneficial, such as in combatting medical conditions wherein inhibition of gastrointestinal motility is thought to be of value. Thus they may be of use for example in the treatment of inflammatory bowel disease (IBD) (such as Crohn's disease and ulcerative colitis), irritable bowel syndrome (IBS), non-specific diarrhoea and dumping syndrome.

Accordingly the present invention provides a method of stimulating the "atypical" β-adrenoceptors in the gastrointestinal tract which comprises administering, to an animal in need thereof, a therapeutically effective amount of a compound of the present invention.

In a further aspect the present invention provides methods of inhibiting gastrointestinal motility, treating IBD, treating IBS, treating non-specific diarrhoea and treating gastric emptying in umping syndrome which comprise administering to an animal in need thereof, a therapeutically effective amount of a compound of the present invention.

In a further aspect the present invention provides a process for preparing a compound of the formula (I) or a bioprecursor thereof or a pharmaceutically acceptable salt thereof which process comprises:

a) reacting a compound (III) or (IV) with a compound of the formula (V):

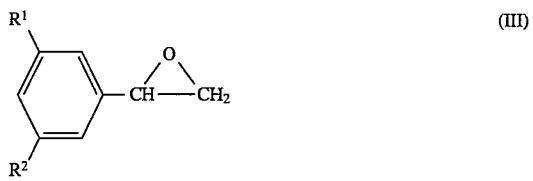

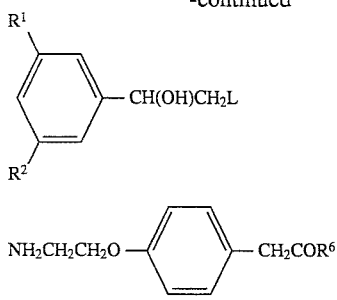
(IV)

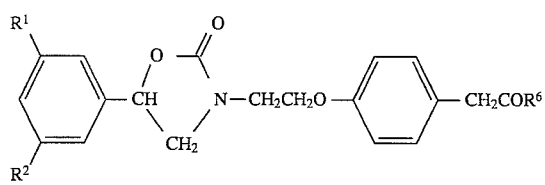
(V)

wherein $R^1$ and $R^2$ are as hereinbefore defined and $-COR^6$ is carboxy or its bioprecursor and L is a displaceable group; or b) hydrolysis of a compound of the formula (VI):

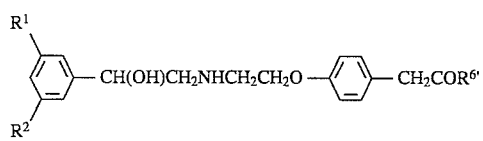
(VI)

wherein $R^1$, $R^2$ and $-COR^6$ are as hereinbefore defined; or c) for forming compounds of the formula (I) hydrolysing a compound of the formula (VII):

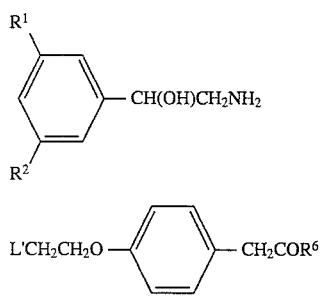
(VII)

wherein $R^1$ and $R^2$ are as hereinbefore defined and $R^{6'}$ is a hydrolysable group;

d) reacting a compound of the formula (VIII) with a compound of the formula (IX):

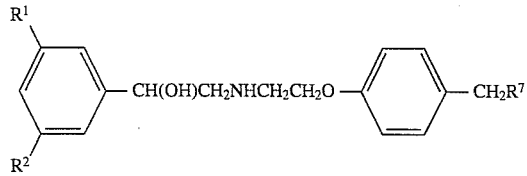
(VIII)

(IX)

wherein $R^1$, $R^2$ and $-COR^6$ are as hereinbefore defined and L' is a displaceable group;

e) deprotecting a compound of the formula (X):

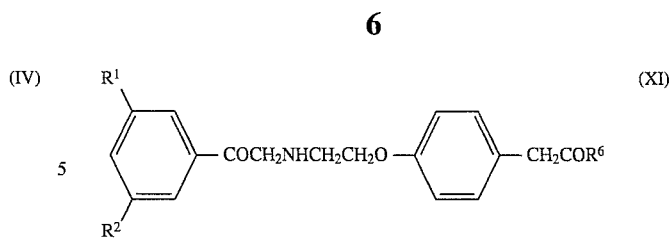
(X)

wherein $R^1$ and $R^2$ are as hereinbefore defined and $R^7$ is a protected derivative of a group $-COR^6$;

f) converting a compound of the formula (I) into a bioprecursor, or vice versa, or converting a bioprecursor of a compound of the formula (I) into another bioprecursor of a compound of the formula (I);

g) reducing a compound of the formula (XI);

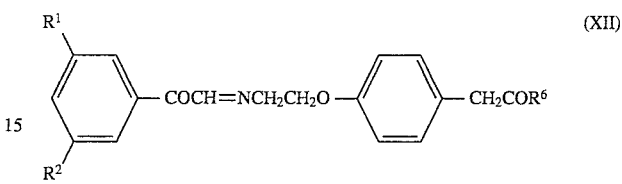
(XI)

wherein $R^1$, $R^2$ and $-COR^6$ are as hereinbefore defined;

h) reducing a compound of the formula (XII):

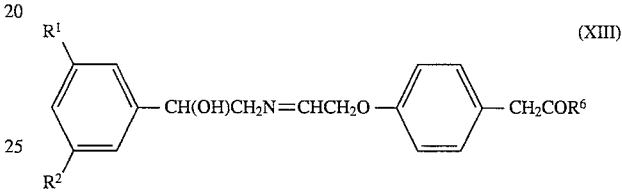
(XII)

wherein $R^1$, $R^2$ and $-COR^6$ are as hereinbefore defined;

i) Reducing a compound of the formula (XIII):

(XIII)

wherein $R^1$, $R^2$ and $-COR^6$ are as hereinbefore defined; and wherein any functional group is optionally protected and thereafter if necessary;

(i) removing any protecting groups;
(ii) forming a pharmaceutically acceptable salt.

Protecting groups may in general be chosen from any of the groups described in the literature or known to the skilled chemist as appropriate for the protection of the group in question, and may be introduced by conventional methods.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

A particular protecting group is a hydrogenolysable group present on the nitrogen atom of $-CH(OH)CH_2NCH_2CH_2O-$. Suitably the protecting group is benzyl or a substituted benzyl group. Such a protecting group may be removed in conventional manner using methods of catalytic hydrogenation, for example palladium on carbon catalysts in an atmosphere of hydrogen. Suitable conditions include ambient and elevated temperatures and pressures in a solvent such as a $C_{2-6}$-alkanol for example ethanol or propan-2-ol. Compounds corresponding to formula (I) protected with a hydrogenolysable group on the nitrogen atom may be prepared by methods analogous to those described above for formula (I).

The reaction between a compound of the formulae (III) or (IV) and a compound of the formula (V) may be performed in a suitable solvent for example an alcohol such as ethanol or propan-2-ol, at a temperature in the range for example 10° C. to 110° C. and most conveniently at or near the boiling-point of the reaction mixture. In the compound of the formula (IV) L may be, for example, halogen such as chloro or bromo or an arylsulphonyloxy group such as toluenesulphonyloxy or an alkanesulphonyloxy group such as methanesulphonyloxy.

The compounds of the formula (V) are prepared in any convenient manner known to those skilled in the art. For example they may be conveniently prepared by reacting compound (XIV) with a compound of the formula (XV):

(XIV)

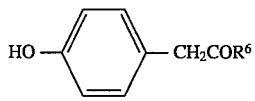
(XV)

For example this reaction may be performed using the Mitsunobu reaction with diethyl azodicarboxylate and triphenylphosphine. Desirably the amino function (and carboxy-function, if present) is protected during this reaction and subsequently deprotected in conventional manner. Examples of a suitable protecting group for the amino function include the phthaloyl and t-butoxycarbonyl groups. The compounds of the formula (XV) may be prepared according to methods known in the art.

The compound of the formula (VI) may be hydrolysed to a compound of the formula (I) or a bioprecursor thereof under conditions known in the beta adrenergic blocker art; for example via alkaline hydrolysis in a suitable solvent.

The compounds of the formula (VI) may be prepared by the reaction of a compound of the formula (XV) with a compound of the formula (XVI):

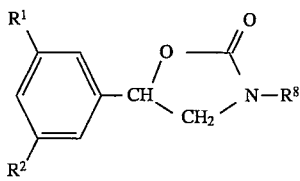
(XVI)

wherein $R^1$ and $R^2$ are as hereibefore defined and $R^8$ is a group —$CH_2CH_2OH$. This reaction may be performed in any conventional manner for example by a method analogous to the reaction of the compounds of the formulae (XIV) and (XV). In an alternative the compounds of the formula (VI) may be prepared by the reaction of a compound of the formula (XVI) wherein $R^8$ is hydrogen with a compound of the formula (IX) as hereinbefore described. In a further alternative the compounds of the formula (VI) may be prepared by the reaction of a compound (III) with a compound of the formula (XVII):

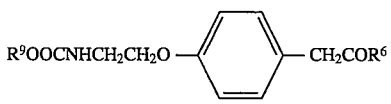
(XVII)

wherein —$COR^6$ is as hereinbefore defined and $R^9O$— is a leaving group, for example $R^9O$— is $C_{1-4}$alkoxy.

The compound of the formula (XVI) wherein $R^8$ is —$CH_2CH_2OH$ may be prepared for example by reaction of a compound of the formula (III) with an N-alkoxycarbonyl derivative of a compound of the formula (XIV) wherein the hydroxy group is optionally protected for example the tetrahydropyranyl ether of t-butoxycarbonylaminoethanol. The compounds of the formula (XVI) wherein $R^8$ is hydrogen are obtainable in conventional manner. The compounds of the formulae (IX) and (XVII) may be obtained by alkylation of the compounds of the formula (XV) in conventional manner.

The reaction between the compounds of the formulae (VIII) and (IX) is conveniently performed under conditions analogous to the reaction between a compound (IV) and a compound of the formula (V). L' may have similar values as recited hereinabove for L.

In the compounds of the formula (VII) examples of hydrolysable groups $R^7$ include $C_{1-6}$ alkoxy and —$NR^3R^4$ groups so that —$COR^7$ represents a $C_{1-6}$alkyl ester or an amide function. Such groups may be hydrolysed (acidic, basic, enzymatic) to a group —COOH under conventional conditions. Conversions wherein $R^7$ is an in vivo hydrolysable group also represent examples of interconversions of a bioprecursor of a compound of the formula (I) into a compound of the formula (I). Suitable acid conditions are for example a strong mineral acid such as hydrochloric, sulphuric or phosphoric acid, conveniently at a temperature in the range, for example, 20° to 110° C. and in a polar solvent, such as water, a $C_{1-4}$alkanol (for example methanol or ethanol) or acetic acid. In such cases, the corresponding mineral acid salt of a compound of the formula (I) may be conveniently isolated. Alternatively, base conditions may be used, for example lithium, sodium or potassium hydroxide, conveniently in a suitable solvent or diluent such as an aqueous $C_{1-4}$alkanol at a temperature in the range, for example, 10° to 110° C.; or an alkali halide for example lithium chloride in a polar solvent such as dimethylsulphoxide. As yet further alternatives, when —$COR^7$ is t-butoxycarbonyl, the decomposition may be carried out, for example, by thermolysis at a temperature in the range, for example, 100° to 220° C., alone or in the presence of a suitable diluent such as diphenyl ether.

The compounds of the formula (VII) may be prepared by methods analogous to those described hereinabove for a compound of the formula (I) or a bioprecursor thereof, with optional protection of the amino function for example with a benzyl group.

Compounds of the formula (I) and amide bioprecursors thereof may be converted to ester precursors thereof. Suitable conditions are, for example, refluxing in the corresponding alkanol under acidic conditions, for example, with the addition of concentrated sulphuric acid as a catalyst.

The reduction of the compounds (XI), (XII) and (XIII) may be carried out by conventional chemical or catalytic methods, such as chemical reduction using sodium borohydride or by catalytic hydrogenation using catalysts such as palladium on charcoal, or platinum.

Reduction by sodium borohydride is conveniently carried out in an alcohol such as methanol and the reaction is generally carried out at from 0°–20° C.

Catalytic reduction is conveniently carried out in a conventional hydrogenation solvent such as an alcohol, for example ethanol. The hydrogenation is generally carried out under hydrogen gas at about 1 to about 10 atmosphere pressure and at ambient or elevated temperature.

Compounds of the formula (XI) may be prepared by the reaction of a compound of the formula (V) with a compound of the formula (XVIII):

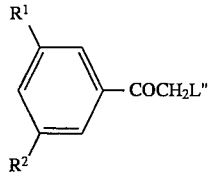
(XVIII)

wherein $R^1$ and $R^2$ are as hereinbefore defined and L" is a displaceable group.

The reaction between a compound of the formula (XVIII) and a compound of the formula (V) may be performed in a suitable solvent such as an alcohol or an ether, for example methanol or diethyl ether, at a temperature in the range, for example, −10° to 110° C. and most conveniently at ambient temperature. In the compounds of the formula (XVIII), L" may be, for example, halogen such as chloro or bromo.

The resulting compounds of the formula (XI) may be converted into a compound of the formula (I) or bioprecursors thereof in situ.

The compounds of the formula (XVIII) may be prepared by methods known in the art.

Compounds of the formula (XII) may be prepared by reacting a compound (XIX) with a compound of the formula (V):

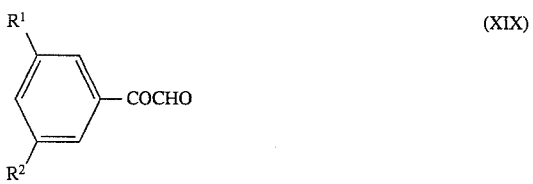

The reaction between a compound (XIX) with a compound of the formula (V) may be performed in a suitable solvent such as an alcohol, for example, ethanol at a temperature range, for example, 0°–80° C. and most conveniently at ambient temperature. The resulting compounds of the formula (XII) may be converted into compounds of the formula (I) or bioprecursors thereof in situ.

Compounds of the formula (XIII) may be prepared by reacting compounds of the formula (XX) with a compound of the formula (VIII):

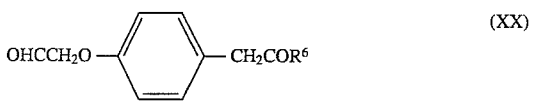

wherein $R^6$ is as hereinbefore defined.

The reaction between a compound of the formula (XX) and a compound (VIII) may be performed in a suitable solvent such as an alcohol, for example, ethanol, at a temperature in the range, for example, 0°–80° C. and most conveniently at ambient temperature. The resulting compounds of the formula (XIII) may be converted into compounds of the formula (I) or bioprecursors thereof in situ.

Compounds of the formula (XX) may be prepared by hydrolysis of a compound of the formula (XXI):

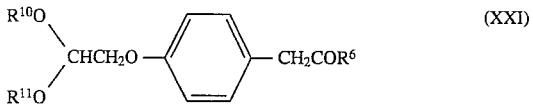

wherein $COR^6$ is as hereinbefore defined and $R^{10}$ and $R^{11}$ are independently hydrogen or $C_{1-4}$alkyl. Suitable conditions for hydrolysis are, for example, a strong mineral acid such as hydrochloric or sulphuric; conveniently at a temperature range, for example, 20°–110° C., in a suitable solvent such as tetrahydrofuran, dichloromethane or diethyl ether.

Compounds of the formula (XXI) may be prepared by standard methods known in the art. For example, by reacting a compound of the formula (XXII) with a compound of the formula (XV) in the presence of a mild base:

wherein $R^{10}$ and $R^{11}$ are as hereinbefore defined and $L'''$ is a displaceable group.

Suitable conditions include heating in a suitable solvent such as dichloromethane, in the presence of a mild base, for example sodium carbonate. In a compound of the formula (XXII) $L'''$ may be, for example, halogen such as bromo.

The compounds of the formulae (VI), (VII), (X), (XI), (XII) and (XIII) are novel and form another aspect of the invention.

Bioprecursor esters of the hydroxy group may be prepared in conventional manner for example by reacting the hydroxy group with an activated derivative of an acid under conditions known in the beta adrenergic blocker art.

Pharmaceutically acceptable salts may be prepared by reacting a compound of the formula (I) or a bioprecursor thereof with the appropriate acid or base in conventional manner. Alternatively when a hydrogen halide salt is required, it may conveniently be obtained by hydrogenation of the free base together with a stoichiometric amount of the corresponding benzyl halide.

The following biological test methods, data and Examples serve to illustrate this invention.

Thermogenic Effects

The thermogenic effects of compounds of the formula (I) and bioprecursors thereof may be demonstrated using one or more of the following standard tests:

(a) Rats are cold adapted at 4° C. for 5 days to increase their capacity for thermogenesis. They are then transferred to a warm environment of 25° C. for 2 days. On the following day, a test compound is administered sub-cutaneously or orally. Animals are sacrificed one hour later and the interscapular, brown adipose tissue (BAT) pad is removed. BAT mitochondria are prepared by differential centrifugation and GDP binding is determined (Holloway et al., *International Journal of Obesity*, 1984, 8, 295) as a measure of thermogenic activation. Each test includes a control which is dosed with the solution/suspension vehicle only and a positive control which is dosed with isoprenaline (as its sulphate) at 1 mgkg$^{-1}$. Test compounds are routinely dosed at 0.1, 0.3, 1.0, 3.0, and 10 mgkg$^{-1}$ and results expressed in terms of the effect on GDP binding produced by the positive control. From these results, a dose ($ED_{50}$) necessary to produce 50% of the isoprenaline effect is calculated by curve fitting. Compounds are considered active in this test if they cause a significant elevation in GDP binding as compared to controls.

(b) Rats are adapted to a thermoneutral environment (29° C.) for 2 weeks in order to decrease their capacity for BAT mediated non-shivering thermogenesis. During the final 5 days the animals are trained to use an apparatus for measuring heart rate non-invasively via foot-pad electrodes connected to an ECG integrator giving a continuous read-out of heart rate. A test compound is administered sub-cutaneously or orally at the $ED_{50}$ determined in test (a), and heart rate is determined 15-30 minutes after dosing. The procedure is then repeated in subsequent tests using increasing multiples of the $ED_{50}$ determined in test (a) until the heart rate (HR) reaches or exceeds 500 beats per minute, or until the dose reaches 100 times the $ED_{50}$ determined in test (a). The dose necessary to produce a heart rate of 500 beats per minute ($D_{500}$ dose) is estimated.

The ratio of $D_{500}$ to $ED_{50}$ in test (a) can be defined as the selectivity index (SI) and provides a measure of the selectivity of the compound for BAT as opposed to the cardiovascular system. Compounds are considered to have significant selectivity which have an SI of >1. Non-selective compounds have an SI of <1 (for example isoprenaline= 0.06).

(c) Rats are kept at 23° C. for at least two days, then fasted overnight. On the following day, the basal metabolic rate of the animals is determined using a close-circuit oxygen consumption apparatus of the type described by Arundel et al., 1984, *J. Appl. Physiol. Respirat. Environ. Exercise*

*Physiol.*, 1984, 57 (5) 1591–1593. The rats are then dosed (orally) with test compound at about 1 mgkg$^{-1}$ as a solution or suspension in 0.025% w/v Polysorbate 80 (0.5 ml/100 g). Metabolic rate is then determined for at least one hour after dosing. Compounds are considered active in this test if they cause a significant increase in metabolic rate as compared to control animals (Student's t test: p<0.05) dosed only the solution or suspension vehicle.

In the above tests, the compounds of the formula (I) in general produce effects of the following order without producing overt toxicity:

test (a): sub-cutaneous or oral ED$_{50}$ for GDP binding in BAT mitochondria of 0.01–10 mgkg$^{-1}$;

test (b): show an SI of >50; and test (c): show 2–9 ml O$_2$ min$^{-1}$(Kg$^{0.75}$)$^{-1}$ at 1mgkg$^{-1}$ p.o.

By way of illustration, the compound described in the accompanying Example 2, produces the following effects in the above tests:

(a) oral ED$_{50}$ 0.75 mgkg$^{-1}$;

(b) SI>50 (oral);

(c) 6.57 ml O$_2$ min$^{-1}$ (Kg$^{0.75}$)$^{-1}$ at 1 mgkg$^{-1}$ p.o.

The invention will now be illustrated by the following Examples in which, unless otherwise stated:

a) chromatography was performed on Kieselgel (Art 9385; 230–400 Mesh) obtainable from E. Merck, Darmstadt, Federal Republic of Germany.

b) evaporations were carried out under reduced pressure using a rotary evaporator.

c) melting-points are uncorrected.

EXAMPLE 1

(R)-Methyl 4-[2-(2-hydroxy-2-(3-trifluoromethylphenyl)ethylamino)ethoxy]phenylacetate (R)-4-[2-(2-Hydroxy-2-(3-trifluoromethylphenyl)ethylamino)ethoxy]phenylacetamide hydrochloride (1.6 g) was heated under reflux in methanol (120 ml) containing concentrated sulphuric acid (1.5 ml) for 18 hours. The mixture was cooled and the solvent evaporated under reduced pressure. The residue was dissolved in dichloromethane (500 ml) and washed successively with water (2×75 ml), brine (75 ml), dried over MgSO$_4$, and the solvent removed under reduced pressure. The residue (0.8 g) was dissolved in methyl acetate (20 ml) and treated with a solution of ether saturated with hydrogen chloride. The precipitated solid was crystallised from a mixture of methanol and methyl acetate to give (R)-methyl 4-[2-(2-hydroxy-2-(3-trifluoromethylphenyl)ethylamino)ethoxy]phenylacetate hydrochloride (0.25 g), m.p. 165°–166° C.; microanalysis: found C, 55.4; H, 5.4; N, 3.2; Cl, 8.2%; required for C$_{20}$H$_{23}$ClF$_3$NO$_4$:C, 55.4; H, 5.3; N, 3.2; Cl, 8.2% [α]$^{25}_D$=−20.7° (c=1.0 in methanol).

(R)-4-[2-(2-Hydroxy-2-(3-trifluoromethylphenyl)ethylamino)ethoxy]phenylacetamide hydrochloride used as a starting material was prepared as follows:

A mixture of 4-[2-(benzylamino)ethoxy]phenylacetamide (OLS 2135678) (3.2 g), (R)-3-trifluoromethylstyrene oxide (European Patent 40,000: preparation 6, p44) and ethanol (125 ml) were heated under reflux for 72 hours to give (R)-4-[2-(N-benzyl-N-(2-hydroxy-2-(3-trifluoromethylphenyl)ethyl)amino)ethoxy]phenylacetamide. The solution was cooled and glacial acetic acid (20 ml) was added. This solution was hydrogenated in the presence of 10% w/w palladium on carbon (0.4 g) at about 20 bars and 60° C. for 48 hours. The mixture was cooled, filtered and the filtrate was evaporated under reduced pressure. The residual oil was dissolved in methanol (10 ml) and treated with a solution of ether saturated with hydrogen chloride. The precipitated solid was crystallised from a mixture of methanol and methyl acetate to give (R)-4-[2-(2-hydroxy-2-(3-trifluoromethylphenyl)ethylamino)ethoxy]phenylacetamide hydrochloride (0.25 g), m.p. 232°–234° C.; microanalysis found C, 54.9; H, 5.5; N, 6.9; Cl, 8.7%: required for C$_{19}$H$_{22}$ClF$_3$N$_2$O$_3$: C, 54.5; H, 5.3; N, 6.7; Cl, 8.5%; [α]$^{25}_D$= −18.2° (c=1.0 in methanol).

EXAMPLE 2

(R)-4-[2-(2-Hydroxy-2-(3-trifluoromethylphenyl)ethylamino)ethoxy]phenylacetic acid (R)-4-[2-(2-Hydroxy-2-(3-trifluoromethylphenyl)ethylamino)ethoxy]phenylacetamide hydrochloride (1.8 g) was heated on the steam bath for 3 hours in 4N HCl (20 ml). The reaction mixture was cooled and the solid collected by filtration. The solid was crystallised from water to give (R)-4-[2-(2-hydroxy-2-(3-trifluoromethylphenyl)ethylamino)ethoxy]phenylacetic acid as the hydrochloride (1.0 g), m.p. 170°–172° C.; microanalysis: found C, 54.8; H, 5.1; N, 3.3; Cl, 8.4%: required for C$_{19}$H$_{21}$ClF$_3$NO$_4$: C, 54.4; H, 5.0; N, 3.3; Cl, 8.4%; [α]$^{25}_D$=−18.7° (c=1.0 in methanol).

EXAMPLE 3

Methyl 4-[2-(2-[3-chlorophenyl]-2-hydroxyethylamino)ethoxy]phenylacetate

4-[2-(2-[3-Chlorophenyl]-2-hydroxyethylamino)ethoxy]phenylacetamide hydrochloride (2.6 g) was heated under reflux in methanol (60 ml) containing concentrated sulphuric acid (2.0 ml) for 18 hours. The mixture was cooled and the solvent evaporated under reduced pressure. The residue was dissolved in dichloromethane (50 ml) and washed successively with water (10 ml), 5% sodium bicarbonate solution (2×20 ml), brine (10 ml), dried over MgSO$_4$, and the solvent removed under reduced pressure. The residual viscous oil (1.9 g) was dissolved in methyl acetate (30 ml) and treated with a solution of ether saturated with hydrogen chloride. The precipitated solid was crystallised from a mixture of methanol and methyl acetate to give methyl 4-[2-(2-[3-chlorophenyl]-2-hydroxyethylamino)ethoxy]phenylacetate hydrochloride, m.p. 139°–141° C.; microanalysis: found C, 56.8; H, 5.8; N, 3.5; Cl, 17.6%; required for C$_{19}$H$_{23}$Cl$_2$NO$_4$: C, 57.0; H, 5.8; N, 3.5; Cl, 17.7%.

4-[2-(2-[3-Chlorophenyl]-2-hydroxyethylamino)ethoxy]phenylacetamide hydrochloride used as a starting material was prepared as follows:

A mixture of 3-chlorophenylglyoxal hydrate (2.79 g), 4-(2-aminoethoxy)phenylacetamide hydrochloride (2.31 g) and triethylamine (1.01 g) was heated in methanol (100 ml) to obtain a solution. This solution was then stirred and cooled in an ice-bath while sodium borohydride (1.5 g) was added in small portions during 1 hour. Stirring was continued for 18 hours and then the solvent was evaporated under reduced pressure. The residue was dissolved in dichloromethane (200 ml) and washed with water (50 ml). The aqueous layer was separated and extracted with dichloromethane (50 ml). The combined dichloromethane extracts were washed with water (2×30 ml), dried over MgSO$_4$, and evaporated. The residual solid was dissolved in ethyl acetate and treated with a solution of ether saturated with hydrogen chloride. The precipitated solid was crystallised from a mixture of methanol and ethyl acetate to give 4-[2-(2-[3- chlorophenyl]-2-hydroxyethylamino)ethoxy]phenylacetamide hydrochloride (0.89 g), m.p. 239°–241° C.; microanalysis: found C, 56.1; H, 5.8; N, 7.4; Cl, 17.9%; required for $C_{18}H_{22}Cl_2N_2O_3$: C, 56.1; H, 5.8; N, 7.3; Cl, 18.4%.

EXAMPLE 4

4-[2-(2-[3-Chlorophenyl]-2-hydroxyethylamino)ethoxy]phenylacetic acid

4-[2-(2-[3-Chlorophenyl]-2-hydroxyethylamino)ethoxy]phenylacetamide hydrochloride (0.6 g) was heated on the steam bath for 3 hours in 2N HCl (30 ml) and then the hot solution was filtered. The solution was cooled and the solid which separated was collected and recrystallised from water to give 4-[2-(2-[3-chlorophenyl]-2-hydroxyethylamino)ethoxy]phenylacetic acid as the hydrochloride (0.32 g), m.p. 180°–182° C.; microanalysis: found C, 55.7; H, 5.4; N, 3.6; Cl, 18.3%; required for $C_{18}H_{21}Cl_2NO_4$: C, 56.0; H, 5.5; N, 3.6; Cl, 18.4%.

EXAMPLE 5

Methyl 4-[2-(2-[3-fluorophenyl]-2-hydroxyethylamino)ethoxy]phenylacetate hydrochloride 4-[2-(2-[3-Fluorophenyl]-2-hydroxyethylamino)ethoxy]phenylacetamide hydrochloride (0.9 g) was heated under reflux in methanol (30 ml) containing concentrated sulphuric acid (0.5 ml) for 18 hours. The mixture was cooled and the solvent evaporated under reduced pressure. The residue was dissolved in dichloromethane (50 ml) and washed successively with 5% sodium bicarbonate solution (2×30 ml), water (10 ml), dried over MgSO$_4$, and the solvent removed under reduced pressure. The residual solid (0.6 g) was dissolved in methyl acetate (10 ml) and treated with a solution of ether saturated with hydrogen chloride. The precipitated solid was crystallised from a mixture of methanol and methyl acetate to give methyl 4-[2-(2-[3-fluorophenyl]-2-hydroxyethylamino)ethoxy]phenylacetate hydrochloride (0.4 g), m.p. 159°–161° C.; microanalysis: C, 59.4; H, 6.0; N, 3.7; Cl; 9.0% required for $C_{19}H_{23}ClFNO_4$: C, 59.5; H, 6.0; N, 3.7; Cl, 9.2%.

4-[2-(2-[3-Fluorophenyl]-2-hydroxyethylamino)ethoxy]phenylacetamide hydrochloride used as a starting material was prepared as follows:

A mixture of 3-fluorophenylglyoxal hydrate (3.0 g), 4-(2-aminoethoxy)phenylacetamide hydrochloride (2.7 g) and triethylamine (1.18 g) was heated in ethanol (200 ml) for about 5 minutes to obtain a solution. This solution was then cooled and stirred in an ice-bath while sodium borohydride (3.0 g) was added in small portions during 1 hour. Stirring was continued for 18 hours and then the solvent was evaporated under reduced pressure. The residue was dissolved in dichloromethane (200 ml) and washed with water (200 ml). The aqueous layer was separated and extracted with dichloromethane (20 ml). The combined dichloromethane extracts were washed with water (2×50 ml), dried over MgSO$_4$, and evaporated. The residual solid was dissolved in ethyl acetate and treated with a solution of ether saturated with hydrogen chloride. The precipitated solid was crystallised from methanol to give 4-[2-(2-[3-fluorophenyl]-2-hydroxyethylamino)ethoxy]phenylacetamide hydrochloride (1.5 g) m.p 248°–250° C.; microanalysis: found C, 58.2; H, 6.1; N, 7.6; Cl 9.4%; required for $C_{18}H_{22}ClFN_2O_3$: C, 58.6; H, 6.0; N, 7.6; Cl, 9.6%.

EXAMPLE 6

4-[2-(2-[3-Fluorophenyl]-2-hydroxyethylamino)ethoxy]phenylacetic acid

4-[2-(2-[3-Fluorophenyl]-2-hydroxyethylamino)ethoxy]phenylacetamide hydrochloride (1.0 g) was heated on the steam bath for 2.5 hours in 2N HCl (10 ml) and then the hot solution was filtered. The solution was cooled and the solid which separated was 4-[2-(2-[3-fluorophenyl]-2-hydroxyethylamino)ethoxy]phenylacetic acid as the hydrochloride (0.52 g), m.p. 184°–186° C.; microanalysis: found C, 58.2; H, 5.7; N, 3.8; Cl, 9.2%; required for $C_{18}H_{21}ClFNO_4$: C, 58.5; H, 5.7; N, 3.8; Cl, 9.6%.

EXAMPLE 7

Methyl 4-[2-(2-[3-bromophenyl]-2-hydroxyethylamino)ethoxy]phenylacetate

4-[2-(2-[3-Bromophenyl]-2-hydroxyethylamino)ethoxy]phenylacetamide hydrochloride (1.0 g) was heated under reflux in methanol (250 ml) containing concentrated sulphuric acid (2.0 ml) for 20 hours. The mixture was cooled and the solvent evaporated under reduced pressure. The residue was treated with 5% aqueous sodium bicarbonate (100 ml), solid sodium bicarbonate (10 g) was added, and the mixture was extracted with dichloromethane (200 ml and then 50 ml). The combined dichloromethane extracts were washed with water (20 ml), dried over MgSO$_4$, and the solvent removed under reduced pressure. The residual oily solid (1.0 g) was dissolved in methyl acetate (15 ml) and treated with a solution of ether saturated with hydrogen chloride. The precipitated solid was crystallised from a mixture of methanol and methyl acetate to give methyl 4-[2-(2-[3-bromophenyl]-2-hydroxyethylamino)ethoxy]phenylacetate hydrochloride (0.49 g) m.p. 156°–158° C.; microanalysis found C, 51.3; H, 5.2; N, 3.0; Cl, 8.2%; required for $C_{19}H_{23}BrClNO_4$: C, 51.3; H, 5.2; N, 3.2; Cl, 8.0%.

4-[2-(2-[3-Bromophenyl]-2-hydroxyethylamino)ethoxy]phenylacetamide hydrochloride used as starting material was prepared as follows:

A mixture of 3-bromophenylglyoxal hydrate (4.46 g) and 4-(2-aminoethoxy)phenylacetamide (2.5 g) in ethanol (220 ml) was heated for about 10 minutes to obtain a solution. This solution was then stirred and cooled in an ice bath while sodium borohydride (3.9 g) was added in small portions during 1 hour. Stirring was continued for 20 hours and then the solvent was evaporated under reduced pressure. The residue was shaken with dichloromethane (200 ml) and water (200 ml) and the white solid (4.65 g) which separated was isolated by filtration. The solid was dissolved in a mixture of methanol (50 ml) and dichloromethane (450 ml) and the solution treated with a solution of ether saturated with hydrogen chloride. The solid which separated was crystallised from methanol to give 4-[2-(2-[3-bromophenyl]-2-hydroxyethylamino)ethoxy]phenylacetamide hydrochloride (2.72 g), m.p. 232°–235° C.; microanalysis: C, 50.1; H, 5.0; N, 6.5; Cl, 8.5%; required for $C_{18}H_{22}BrClN_2O_3$: C, 50.3; H, 5.2; N, 6.5; Cl, 8.25%.

EXAMPLE 8

4-[2-(2-[3-Bromophenyl]-2-hydroxyethylamino)ethoxy]phenylacetic acid

4-[2-(2-[3-Bromophenyl]-2-hydroxyethylamino)ethoxy]phenylacetamide hydrochloride (1.4 g) was heated on the steam bath for 5 hours in water (25 ml) containing 37% hydrochloric acid (12.5 ml). A further amount of water (50 ml) was added, the hot solution was filtered and allowed to cool. The solid which separated was crystallised from water and gave 4-[2-(2-[3-bromophenyl]-2-hydroxyethylamino)ethoxy]phenylacetic acid as the hydrochloride (0.4 g), m.p. 179°–182° C.; microanalysis: found C, 50.4; H, 5.0; N, 3.2; Cl, 8.1%; required for $C_{18}H_{21}BrClNO_4$: C, 50.2; H, 4.9; N, 3.25; Cl, 8.2%.

EXAMPLE 9

4-[2-(2-[3,5-Difluorophenyl]-2-hydroxyethylamino)ethoxy]phenylacetic acid

Using a similar procedure to that described in Example 6, there was obtained 4-[2-(2-[3,5-difluorophenyl]-2-hydroxyethylaminoethoxy]phenylacetic acid as the hydrochloride, m.p. 197°–198° C., microanalysis found; C, 55.7; H, 5.3; N, 4.0; Cl, 8.7%; required for $C_{18}H_{20}ClF_2NO_4$: C, 55.7; H, 5.2; N, 3.6; Cl, 9.1%.

The starting material was prepared as follows:

4-[2-Aminoethoxy]phenylacetamide (1.94 g) was suspended in methanol (30 ml) and added to a stirred solution of 3,5-difluorophenylglyoxal hydrate (2.55 g) in methanol (30 ml). The mixture was warmed on a steam bath until a clear solution was obtained, diluted with further methanol (30 ml) and cooled to 0° C. Sodium borohydride (3×0.4 g tablets (Aldrich) 31.5 mmol) was added over 15 minutes maintaining the temperature at 0°–5° C. The mixture was stirred overnight and allowed to attain room temperature.

The methanol was evaporated under reduced pressure and the resultant white solid was shaken with water (20 ml) and dichloromethane (30 ml). The slurry thus formed was filtered and the solid obtained, washed with water until the washings were no longer alkaline. There was thus obtained 4-[2-(2-[3,5-difluorophenyl]-2-hydroxyethylamino)ethoxy]phenylacetamide (2.75 g), m.p. 132°–133° C.

EXAMPLE 10

4-[2(2-Hydroxy-2-(3-methylphenyl)ethylamino)ethoxy]phenylacetic acid

Using a similar procedure to that described in Example 6, there was obtained 4-[2-(2-hydroxy-2-(3-methylphenyl)ethylamino)ethoxy]phenylacetic acid as the hydrochloride, m.p. 177°–178° C., microanalysis: found C, 62.1; H, 6.7; N, 4.0; Cl, 9.8%; required for $C_{19}H_{24}NO_4Cl$: C, 62.4; H, 6.6; N, 3.8; Cl, 9.7%.

The starting material 4-[2-(2-hydroxy-2-(3-methylphenyl)ethylamino)ethoxy]phenylacetamide, m.p. 146°–147° C., was obtained in analogous manner to that for the starting material in Example 9 using 3-methylphenylglyoxal hydrate as the initial reagent.

EXAMPLE 11

As stated previously, suitable pharmaceutical compositions of compounds of formula (I) defined hereinbefore may be obtained by standard formulation techniques.

A typical tablet formulation suitable for oral administration to warm-blooded animals comprises as active ingredient a compound of formula (I), or a pharmaceutically acceptable salt thereof, as defined hereinbefore (for example as described in one of the preceding Examples), and may be produced by aqueous granulation or direct compression together with milled lactose containing a standard disintegrant and/or lubricant. When tablets containing small amounts of active ingredient (for example 0.5–10 mg) are required, the direct compression method may be used wherein the active ingredient is mixed with lactose in the ratio of 1:10 parts by weight and/or microcrystalline cellulose containing 0.5% by weight of a lubricant (such as magnesium stearate) and 5% by weight of a disintegrant (such as cross-linked sodium carboxymethyl cellulose or sodium starch glycolate). An example of a tablet prepared by aqueous granulation is that containing active ingredient (50–100 mg), lactose (230 mg), maize starch (80 mg), gelatine (2.2 mg), magnesium stearate (4 mg) and croscarmellose sodium (7 mg).

EXAMPLE 12

(R)-4-[2-(2-[3-Chlorophenyl]-2-hydroxyethylamino)ethoxy]phenylacetic acid (R)-4-[2-(2-[3-Chlorophenyl]-2-hydroxyethylamino)ethoxy]phenylacetamide (4 g) was heated on the steam bath for 3 hours in 2N HCl (24 ml) and water (40 ml). After 15 minutes water (20 ml) was added to the suspension which gradually formed a solution. The solution was stirred for a total of 135 minutes and cooled. The crystals which formed were collected to provide (R)-4-[2-(2-[3-chlorophenyl]-2-hydroxyethylamino)ethoxy]phenylacetic acid as the hydrochloride (3.2 g), m.p. 191° C.; microanalysis: found C, 56.0; H, 5.9; N, 3.5; Cl, 18.4%; required for $C_{18}H_{21}Cl_2NO_4$: C, 56.0; H, 5.5; N, 3.6; Cl, 18.4%. $[\alpha]_D = -24.6$ (c=1.0 in methanol) (determined on material from a second similar experiment).

(R)-4-[2-(2-[3-Chlorophenyl]-2-hydroxyethylamino)ethoxy]phenylacetamide used as a starting material was prepared as follows:

A mixture of (R)-3-chlorostyrene oxide (17.72 g) and 4-(2-aminoethoxy)phenylacetamide (22.24 g) was heated in ethanol (400 ml) and stirred under reflux, in an argon atmosphere, for 72 hours. The resultant solution was cooled and evaporated under reduced pressure. The residue was slurried, with ultrasound, in dichloromethane (150 ml) to give a fine suspension. This was filtered and the filtrate was subjected to chromatography on silica (grade 9385) (500 g) eluting with 5% methanol in dichloromethane. The appropriate fractions were combined and evaporated to provide (R)-4-[2-(2-[3-chlorophenyl]-2-hydroxyethylamino)ethoxy]phenylacetamide (13.6 g), m.p. 146° C. (determined on material from a second similar experiment).

We claim:

1. A compound of the formula (I):

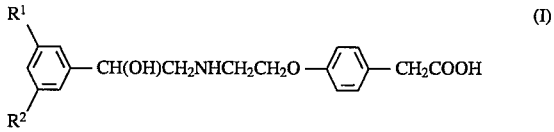

wherein $R^1$ is chloro, fluoro, bromo, trifluoromethyl or methyl; $R^2$ is hydrogen or fluoro; or a bioprecursor or a pharmaceutically acceptable salt thereof.

2. A compound according to claim 1 wherein $R^1$ is chloro, fluoro or bromo and $R^2$ is hydrogen.

3. A compound according to claim 1 wherein $R^1$ is chloro and $R^2$ is hydrogen.

4. A compound according to any one of claims 1, 2 and 3 when in the form of a carboxylic acid or pharmaceutically acceptable salt thereof.

5. A compound according to claim 4 in the form of a salt formed with hydrochloric acid.

6. A compound according to claim 1 which is (R)-4-[2-(2-(3-chlorophenyl)-2-hydroxyethylamino)ethoxy]phenylacetic acid or a pharmaceutically acceptable salt thereof.

7. A compound according to claim 1 which is a salt of (R)-4-[2-(2-(3-chlorophenyl)-2-hydroxyethylamino)ethoxy]phenylacetic acid formed with hydrochloric acid.

8. A pharmaceutical composition which comprises a compound according to claim 6 or claim 7, or a bioprecursor or pharmaceutically acceptable salt thereof and a pharmaceutically acceptable carrier.

9. A pharmaceutical composition which comprises a compound according to claim 1 or a bioprecursor or pharmaceutically acceptable salt thereof and a pharmaceutically acceptable carrier.

* * * * *